United States Patent [19]

Weidlich

[11] Patent Number: 5,216,255
[45] Date of Patent: Jun. 1, 1993

[54] BEAM PROFILE GENERATOR FOR PHOTON RADIATION

[75] Inventor: Georg A. Weidlich, Concord, Calif.

[73] Assignee: Siemens Medical Laboratories, Concord, Calif.

[21] Appl. No.: 860,959

[22] Filed: Mar. 31, 1992

[51] Int. Cl.[5] ............................................. G21K 1/04
[52] U.S. Cl. .............................. 250/492.3; 250/505.1; 378/148; 378/150; 378/151; 378/152
[58] Field of Search ............... 250/492.3, 503.1, 505.1; 378/65, 148, 150, 151, 152, 153

[56] References Cited

U.S. PATENT DOCUMENTS

| | | | |
|---|---|---|---|
| 4,027,167 | 5/1977 | Pollermann | 378/153 |
| 4,109,154 | 8/1978 | Taumann | 250/503 |
| 4,140,129 | 2/1979 | Heinz et al. | 128/404 |
| 4,343,997 | 8/1982 | Heinz | 250/505.1 |
| 4,359,642 | 11/1982 | Heinz et al. | 378/150 |
| 4,380,820 | 4/1983 | Cutter | 378/153 |
| 4,581,753 | 4/1986 | Rice | 378/150 |
| 4,672,652 | 1/1987 | Hüttenrauch et al. | 378/148 |
| 4,754,147 | 6/1988 | Maughan et al. | 378/152 |
| 4,817,125 | 3/1989 | Sklebitz | 378/150 |
| 5,008,907 | 4/1991 | Norman et al. | 378/65 |
| 5,019,713 | 5/1991 | Schmidt | 250/492.3 |

OTHER PUBLICATIONS

"Automatic Variation of Field Size and Dose Rate in Rotation Therapy", Mantel et al., 2 J. Radiat. Oncol. Biol. Phys. 697 (1977), pp. 697–704.
"Wedge Shaped Dose Distribution by Computer Controlled Collimator Motion", Kijewski et al., 5 Med. Phys. 426 (1978), pp. 426–429.
"Computer Controlled Radiation Therapy", Levene et al., 129 Radiol. 769, (1978), pp. 769–775.
"Dose Optimization with Computer Controlled Gantry Rotation, Collimator Motion and Dose Rate Variation", Chin et al., 9 J. Radiat. Oncol. Biol. Phys. 723 (1983), pp. 723–729.

*Primary Examiner*—Paul M. Dzierzynski
*Assistant Examiner*—Kiet T. Nguyen
*Attorney, Agent, or Firm*—Lawrence C. Edelman

[57] ABSTRACT

A system for applying radiation treatment under computer control is disclosed. The system has a radiation source, which generates a variable intensity radiation beam, and a collimator. The collimator has a plurality of movable plates disposed in the path of the radiation beam and is oriented in a direction perpendicular to the beam axis. The apparatus is capable of actuating the plates independently during the radiation treatment, in response to a first control signal. The beam changes in width when the plates are so actuated. The collimator is rotated in response to a second control signal. The intensity of the radiation beam may be varied as a function of the plate position. A total radiation dosage is applied during two intervals. The first interval precedes the collimator rotation, and the second interval follows the rotation.

13 Claims, 5 Drawing Sheets

BEAM PROFILE GENERATOR FOR PHOTON RADIATION

BACKGROUND OF THE INVENTION

1. Field of the Invention

This invention relates to the field of linear accelerators, and in particular to computer controlled radiation therapy systems.

2. Description of the Prior Art

Radiation therapy has been used extensively as a method for treating cancer patients, either alone, or in combination with surgery and chemotherapy. In typical radiation therapy systems, such as the Mevatron systems available from Siemens Medical Systems, Inc. (Iselin, N.J.), a radiation source is housed in a structure called a gantry. The apparatus includes a conventional microwave power source such as a klystron, and an accelerator structure, which may be a travelling wave or standing wave device. The accelerator produces an electron beam, which is steered through a collimating head mounted on the gantry and directed at the region to be treated. For more superficial tumors, the electron beam itself is used for treatment, because it has less impact on deeper tissue. For deeper tumors, however, high energy X rays are preferred for their penetrating power. To generate the X rays, the same electron accelerator may be used with the addition of a target made of heavy metal (e.g., gold or tantalum) placed in the electron beam path. The target emits a continuous X ray Bremsstrahlung spectrum when struck by the electron beam.

The gantry can rotate about a gantry axis which extends from the head to the foot of a treatment couch on which the patient lies, so that the radiation can enter the patient from different angles. The radiation beam coming from the accelerator is always directed through, and centered on, the gantry axis.

In applying radiation to the patient, two competing objectives are present: eliminating the malignant cells in the target region, and avoiding complications due to application of radiation to surrounding tissues. To avoid these complications, lower doses have often been applied to the targeted tumor cells than would be applied if complications were not considered, lowering the probability of successful cancer elimination. To protect surrounding tissues without compromising the treatment, it is desirable to tailor the radiation dosage to match the size, shape and location of the malignant region.

Several methods have been used in radiation therapy systems to improve control of the dosage distribution. One such method is to shape the beam profile. The "raw" beam which leaves the target has a non-uniform intensity. It is known to balance or compensate the dosage in any given space-angle rang of the radiation leaving the target by placing a compensating absorber in the beam path. U.S. Pat. No. 4,109,154 to Taumann discusses an electron accelerator in which a compensating absorber is used to shape the beam profile. The absorber absorbs overly intense radiation in the center of the beam cone.

A paper by Mantel, et al. entitled "Automatic Variation of Field Size and Dose Rate in Rotation Therapy," 2 J. Radiat. Oncol. Biol. Phys. 697 (1977) discusses a technique for changing the field size and dose rate used during rotation therapy. The gantry (and the enclosed beam forming head) rotates around the patient, so that the beam is applied from several angles. The field size and dose rate are varied as functions of the gantry angle. In this technique, the field size is adjusted in one dimension by moving a set of collimator aperture plates, or jaws, which define the beam aperture (and control the beam width), and simultaneously varying the dose rate during rotation in accordance with values selected by a computer program. The result is a more uniform dose distribution inside the target volume, and reduced dose outside that volume.

U.S. Pat. No. 4,140,129 to Heinz et al discloses a beam defining system for an electron accelerator, having an adjustable collimator and an accessory holder, to which an electron applicator is attached. The electron applicator has an wall which encloses the electron beam cone from the collimator, and an additional frame-shaped limiting aperture in order to limit the electron beam cone at the edges which face away from the beam defining system. The scattered or secondary electrons in the marginal region of the beam cone are substantially blocked by the limiting aperture. The electrons which are thus blocked have lower energy levels and, so, do not contribute to higher dosage performance deep within the patient. Thus, this device reduces undesirable irradiation of the skin surrounding the target.

U.S. Pat. Nos. 4,343,997 and 4,359,642 to Heinz, which are hereby incorporated by reference for their teachings on radiation treatment devices, describe a collimator assembly which may be used to limit or define X-ray cones of various sizes in an electron beam accelerator. A flattening filter is used with the technique to flatten the X-ray density profile. Flat dosage is achieved through the use of a collimator shielding block and one of a plurality of insert pieces or bushings which are interchangeable with one another to produce different cone angles for irradiating differently sized areas.

Another method of controlling the dosage profile is to vary the size of the beam aperture. A paper by Kijewski, et al. entitled "Wedge shaped Dose Distribution by Computer Controlled Collimator Motion" 5 Med. Phys. 426 (1978) discusses the use of a defined plate (jaw) motion to obtain a wedge-shaped isodose curve (the set of points which receive the same dose of radiation) during irradiation. FIG. 2a shows isodose profiles 30a–c achieved by this technique. The treatment begins with two collimator plates 32a, 32b separated from one another. After a predetermined time interval, plate 32a is moved towards plate 32b, which remains stationary. The movement continues until the plates meet. This causes the width of the beam 34 to become narrower as the treatment continues. The isodose curves 30a–c are deeper in the region near the stationary plate, which is exposed to radiation the longest. Such wedge shaped isodose curves may be desired in radiation therapy to adjust to anatomical conditions of the subject. A similar result may be achieved by beginning with closed plates and opening the plates. FIG. 2b shows an isodose curve in which the plates 32c, 32d begin in the closed position.

U.S. Pat. No. 5,019,713 to Schmidt discusses a radiation therapy device in which a movable aperture assembly and a non-movable filter body are combined to allow the isodose curve in the object of irradiation to rise or fall in the opening direction. At the beginning of the treatment, the plates are closed, and one plate begins to move away from the other (stationary) plate. The absorptance of the filter varies across its length. The cumulative radiation dose received at any point varies as a function of both the filter characteristics and the distance from the stationary plate, making possible non-monotonic isodose curves which vary in one dimension. For example, if the portion of the filter closest to the stationary plate has a higher absorptance, the isodose curve will have an inverted U-shape.

A paper by Levene, et al. entitled, "Computer Controlled Radiation Therapy" 129 Radiol. 769 (1978) discusses variation of dose rate, gantry angle and collimator plate position to achieve the known "arc wedge" technique.

A paper by Chin et al. entitled, "Dose Optimization with Computer Controlled Gantry Rotation, Collimator Motion and Dose Rate Variation" 9 J. Radiat. Oncol. Biol. Phys. 723 (1983) discusses a method by which continuous irradiation is simulated by summation of a large number of discrete stationary beams. Dose rate, gantry angle and collimator plate positions are varied among the beams. These methods achieve isodose contours which might not be attainable using a single stationary beam.

It is noted that the Levene et al. and Chin et al. papers relate to a conformal radiation treatment which conforms the field gradient and dose rate to a target volume using gantry rotation.

Although some of these devices allow a number of different isodose contours to be generated, the apparatus and methods used may be relatively cumbersome and time consuming.

SUMMARY OF THE INVENTION

In accordance with the present invention, an exemplary system and method are provided for controlling the isodose profile in a radiation treatment apparatus. The system includes an electron accelerator which generates a photon beam. The accelerator has a collimator assembly operating under computer control. The collimator assembly includes a plurality of movable plates mounted to a rotatable collimating head. The plates are oriented in a direction perpendicular to the longitudinal axis of the beam, so that the width of the beam is defined by the relative positions of the plates.

The plates are actuated during the radiation treatment, under computer control, to vary the beam width defined by the opening formed between the plates. The treatment is divided into two parts. During each part, two movable plates are first moved together from an open position, and then opened from a closed position or vice versa. The direction of motion of the plates during the second part of the treatment is perpendicular to the direction of plate motion during the first part.

According to one aspect of the invention, the apparatus has a single pair of plates which move during the radiation treatment and a rotating collimating head. The collimating head is rotated by ninety degrees between the first and second parts of the treatment.

According to another aspect of the invention, the apparatus has two sets of movable plates, which are movable in orthogonal directions to perform the first and second parts of the treatment.

According to another aspect of the invention, the apparatus includes a radiation beam generator which may be controlled by the computer to generate beams of photons having different intensities.

According to yet another aspect of the invention, the computer is programmable to move the plates and to change the intensity of the photon beam during treatment to produce a arbitrary isodose profile.

BRIEF DESCRIPTION OF THE DRAWINGS

FIG. 1b is a cross-sectional view, taken perpendicular to the beam axis which shows the beam-defining jaws of the system shown in FIG. 1a.

FIGS. 3a and 3b are graphs of radiation intensity versus distance which show exemplary parabolic isodose profiles that may be generated by the apparatus shown in FIG. 1a.

FIG. 4 is a graph of an isodose curve (102) and radiation intensity versus distance (100) which shows the unfiltered beam profile produced by the apparatus shown in FIG. 1a.

FIG. 5a is a graph of an isodose curve which shows a flattened beam profile generated by the system shown in FIG. 1a.

FIGS. 5b and 5c are cross-sectional views, taken perpendicular to the beam axis which show the motion of the beam-defining jaws used to produce the flattened beam profile of shown in FIG. 5a.

DETAILED DESCRIPTION

Figure 1A:
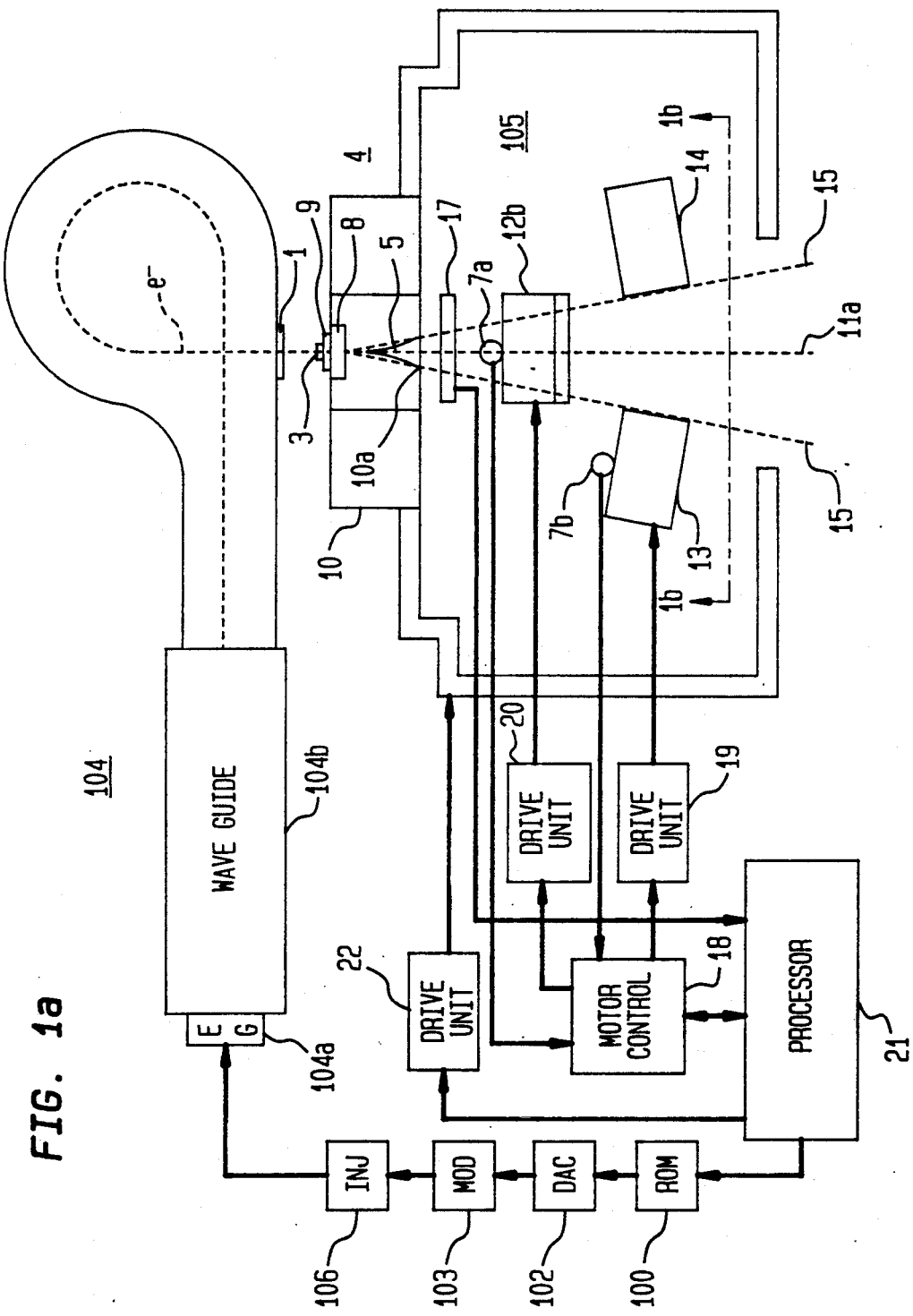
FIG. 1a is a cross-sectional view, partly in block diagram form of radiation treatment apparatus which includes an embodiment of the present invention.

FIG. 1a shows an exemplary embodiment of the beam defining system 6 of a medical linear accelerator in accordance with the present invention. An electron accelerator 104 has an exit window 1, through which an electron beam e⁻ is transmitted to a collimator assembly 105. The collimator assembly 105 includes a target 3 and electron absorber 9 for generating an X ray beam. The generated beam is substantially free of unabsorbed electrons. The target 3 and electron absorber 9 are mounted within a carrier plate 8 of the assembly 105. The target 3, absorber 9 and carrier plate 8 may be removed from the apparatus if desired, to use the electron beam itself for treatment (e.g., for superficial treatment) instead of X rays. The term radiation beam will be used to refer to either an electron beam or an X ray beam.

The intensity of the electron beam and thus of the X ray beam is controlled by the processor 21. In response to address values provided by the processor 21, a read-only memory (ROM) 100 applies programmed digital values to a digital-to-analog converter (DAC) 102. The DAC 102 converts the digital values into control voltage signals for a modulator 103. The modulator, in turn, controls a pulse injector 106 to provide pulses at a rate determined by the control voltage signals to an electron gun 104a of the linear accelerator 104. In response to different control voltage signal values, the linear accelerator produces bursts of electrons at respectively different pulse rates (commonly referred to as PRF). Bursts produced at a relatively high rate generate a more intense beam of radiation (i.e. a higher dose rate) than bursts at a relatively low rate. In the exemplary embodiment of the invention, the processor 21 can change the intensity of the X ray beam during a treatment to generate different beam profiles. The processor 21 monitors the intensity of the beam using a radiation detector 17. This detector 17 may be, for example, a conventional low-density scintillation detector.

The radiation beam has a central move axis 11a. A beam collimating block 4 is disposed in the path of the radiation, directly below the carrying plate 8. The beam collimating block includes a thick walled collimator shielding block or collimator 10. The collimator 10 houses an insert 10a, to which a flattening filter 5 may be mounted. The flattening filter 5, when used, symmetrically attenuates the radiation more towards the center of the beam, so that the intensity of the radiation is approximately constant across the beam width. Filter 5 is rotationally symmetric and is centered relative to axis 11a.

Figure 1B:
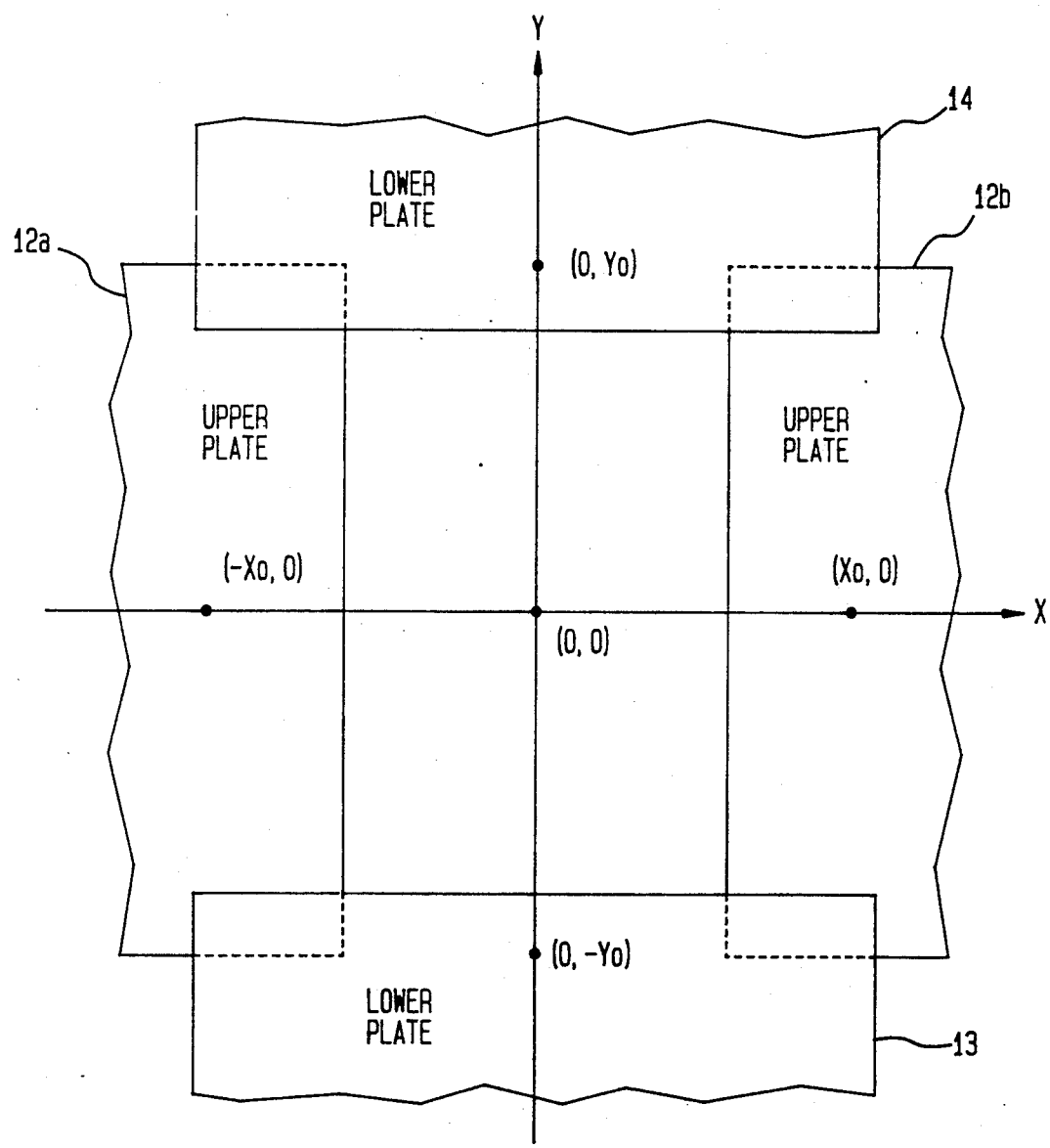

The collimator assembly 105 has two pairs of tungsten X ray shielding plates, 12a, 12b, and 13, 14 which are adjustable relative to the axis 11a. In the system shown in FIG. 1a, plate 12a (not visible in the Figure) moves into the page while plate 12b moves out of the page. Plates 13 and 14 move to the left and right respectively. Thus, each pair of plates 12a, 12b and 13, 14 is movable along a single axis, referred to as the X and Y axes, respectively. The X and Y axes and the beam axis 11a form an orthogonal set. The inner edges of the 25 plates define the radiation field edge, and therefore, the positions of the four plates determine the radiation field size. The plates 12a, 12b, 13 and 14 are shown in a view along the Z axis in FIG. 1b. At least two of the plates are capable of crossing axis 11a. The collimator is mounted for rotation about the beam axis.

In order to provide the desired accuracy for the speed and position of the collimator plates 12, 13, 14, the plate positions are controlled by an automatic drive units 19 and 20 under computer 21 control. Although only two drive units are shown, it is contemplated that each of the plates 12a, 12b, 13 and 14 may have a separate drive unit, each independently controlled by the processor 21. In this configuration, the processor 21 can independently control the position, velocity and acceleration of each plate during a treatment. The drive units 19 and 20 may be, for example, a conventional numerically controlled servo system which may use either conventional servo motors or stepper motors to control the positions of the jaws 12a, 12b, 13 and 14. Feedback on the instantaneous position of the plates 12b and 13 is provided by respective position sensors 7a and 7b. The sensors 7 and 9 may be, for example, conventional resolver units, mounted on the same shaft as the motors of the drive units 20 and 19, respectively.

In the exemplary embodiment of the invention, the computer 21 periodically calculates a desired position for at least one of the jaws 12a, 12b, 13 and 14 and applies the desired positions to the actuators 19 and 20 via actuator control signals. The actuators, in turn, move the jaws to the desired next position. Using this control scheme, a wide variety of beam profiles may be generated which employ both linear and non-linear jaw-motion functions.

In addition, the processor 21 may transmit rotation control signals to cause the entire collimator assembly 105 except for the collimating block 4 to rotate by 90° (i.e. counter-clockwise out of the page) and then back to 0° by activating drive unit 22.

The invention includes an apparatus for producing a beam with an arbitrary two dimensional isodose contour. An isodose contour is the locus of points in three dimensional space which receive the same total dosage of radiation. The isodose contour is the three dimensional analog of the two dimensional isodose curve.

In some of the embodiments of the invention described below, the apparatus used is as described above, with the flattening filter installed in the collimator. With this filter in place, the beam leaving the collimator is of substantially uniform intensity in both the X and Y directions. Other embodiments of the invention produce a substantially flat beam profile without using a flattening filter.

In order to determine the plate movements which result in the desired dosage being applied, a coordinate system is adopted in which the X and Y axes are located in a plane parallel to the surface of the object which is to be irradiated. The Z axis coincides with the longitudinal axis of the beam and the positive Z direction is the direction of the beam (i.e., pointing from the radiation source towards the treatment area). One set of plates moves in a direction parallel to the X axis and the other set of plates moves in the direction parallel to the Y axis. The inventor has determined that for an arbitrary dosage distribution, the plate movements and dosage rate are related by equation (1).

$$\dot{D}_{0(x,y)} = \left| D_a \mu e^{\mu z(x,y)} \left( v_x \frac{d}{dx} [z(x,y)] + v_y \frac{d}{dy} [z(x,y)] \right) \right| \quad (1)$$

where
$z(x,y)$=Depth of isodose contour at (x,y), measured in the z direction
$\dot{D}_{0(x,y)}$=Dose rate deposited at the surface at point (x,y)
$\mu$=Liner attenuation coefficient for the medium irradiated
$D_a$=Dosage on isodose contour
$v_x = dx/dt$=relative plate velocity in the X direction and
$v_y = dy/dt$=relative plate velocity in the Y direction For an isodose contour with an arbitrary shape, the contour $z_{(x,y)}$ will be a function of both X and Y. In order to apply equation (1) for such an isodose contour, the irradiated surface is divided into a two dimensional array of treatment areas, where an independent radiation field is applied to each area.

To apply the radiation to one of these areas, one set of collimator plates 13, 14 is held still, while the plates 12 in the second pair may be moved relative to one another to produce, for example, a wedge shaped area isodose contour. For any area with a flat isodose contour, both sets of plates are held still. For each of these areas, a dosage profile (e.g., constant or wedge shaped) is applied, to approximate the desired isodose contour with a function which is piecewise continuous. This dosage profile may have discontinuities in its derivative at the edges of each treatment area, depending on the profile within each area.

The dosage profile may also be changed by changing the intensity of the beam provided by the linear accelerator 104 and wave guide 2. As set forth above, this occurs when the processor 21 changes the address value applied to the ROM 100, thereby changing the PRF of the bursts applied to accelerator 104.

The method described above for an arbitrary isodose contour may be time consuming if the number of treatment areas is very large. Depending on the nature of the isodose profile in each area, the collimator plates may have to be repositioned when each treatment area is begun. The method is useful, however if extremely tight control of the isodose contour is desired.

The first exemplary embodiment of the invention includes a method for generating a large and useful class of isodose contours for which the number of independent treatment areas is one. That is, the radiation may be applied in a two part treatment consisting of only one set of plate movements in the X direction and one set of movements in the Y direction. While the first pair of plates is moving in the X direction, the plates oriented parallel to the Y axis remain still (i.e., Y=a constant). Similarly, while the second pair of plates is moving in the Y direction, the plates oriented parallel to the X axis remain still (i.e., X=a constant). Further, to simplify the demands made on the equipment configuration, the plate motions are limited so that the plate speed and the beam intensity variations are continuous functions of time within each of the two sections of the treatment. Any contour which can be described by equation (2) falls into this category.

$$z(x,y) = z_1(x) + z_2(y) \tag{2}$$

where:

$z_1(x)$ = a function of x only
$z_2(y)$ = a function of y only

For any desired isodose contour which can be expressed as the sum of a function of only X plus a function of only Y, the treatment can be applied in two distinct parts, one including plate motion in the X direction for a fixed Y direction plate opening, and the other including motion in the Y direction for a fixed X direction plate opening.

An example of such a contour is one in which there is rotational symmetry about the beam axis. For such an isodose contour, any cross section which is perpendicular to the beam axis (i.e., constant depth, z) will be a circle. Such an isodose contour is described by equation (3), in which the locus of points for any fixed value of z define a circle.

$$z(x,y) = C_3 - a * (x^2 + y^2) \text{ for all } x,y \tag{3}$$

In equation (3), the values of $C_3$ and "a" are determined from the boundary conditions for a particular isodose contour. In the exemplary embodiment, $C_3$ is the depth of the isodose curve at beam axis (X=0, Y=0).

In order to apply the treatment, the apparatus is initially set up with flattening filter 5 in place, and the lower collimator plates 13, 14 positioned at edges of the beam field symmetrically placed about the X axis at coordinates (X=0, Y=$-Y_0$) and (X=0, Y=$+Y_0$), respectively, where $Y_0$ is a constant. These plates are held steady during the first section of the treatment, and for the purposes of the treatment, may be considered "fully open." While plates 13 and 14 may be physically capable of opening further, this would result in undesirable irradiation of surrounding tissues.

Upper plate 12a is initially placed along the X axis at (X=$-X_0$, Y=0), where $X_0$ is a constant. Upper plate 12b is placed at the origin (i.e. X=0 and Y=0). Plate 12b is held motionless at the origin, while Plate 12a is moved towards plate 12b at a constant velocity, $v_x$. It is understood that the application of a radiation beam with constant intensity during this motion would result in the known wedge shaped isodose contour. Instead, during this portion of the treatment, the intensity of the beam is controlled by the processor 21 as a function of the position of plate 12a according to equation (4).

$$\dot{D}_{1(x)}|_{y=const.} = D_a \mu b_x e^{\mu(-ax^2+cx)} * (2axv_x) \tag{4}$$

The inventor has determined that this combination of plate motion and radiation intensity produces an isodose contour with the desired parabolic cross section, with the maximum radiation dosage at the origin, and zero dosage at (X=$-X_0$).

Once the two plates meet at the origin, the beam is completely blocked. The irradiation of the half of the treatment area for which X is less than zero is complete for the first half (with Y=a constant) of the treatment. The treatment may optionally be interrupted at this point with no effect on the total dosage received at any point.

During the next portion of the irradiation, plate 12a is held motionless, while plate 12b moves away from plate 12a in the positive X direction. The intensity of the radiation beam during this part of the treatment is again controlled to follow equation (4). The second portion of the irradiation treatment deposits a beam profile on the positive side of the X axis, completing the desired parabolic cross section, with the maximum radiation dosage at the origin, and zero dosage at (X=$+X_0$). When plate 12b reaches the point (X=$+X_0$, Y=0), the radiation is interrupted by, for example, conditioning the accelerator 104 to provide no electron beam pulses or by closing a shutter to block the electron beam $e^-$. The first half of the treatment, in which the positions of plates 13, and 14 are held constant, is complete.

To set up for the second half of the treatment, the upper plate 12a is returned to (X=$-X_0$, Y=0), "fully opening" the upper plates 12a and 12b. These plates will be motionless in the second half of the treatment As in the first half of the treatment, the motionless plates are only opened up enough to irradiate the zone to be treated so that surrounding tissues are not subjected to unnecessary irradiation.

Lower plate 14 is moved to the origin and lower plate 13 is initially left at its open position at (X=0, Y=$-Y_0$). Plate 14 is held motionless at the origin, while Plate 13 is actuated towards plate 14 at a constant velocity $v_y$. During this portion of the treatment, the intensity of the beam is governed by equation (5).

$$\dot{D}_{2(y)}|_{x=const.} = D_a \mu b_y e^{\mu(-ay^2+cy)} * (2ayv_y) \tag{5}$$

This isodose contour has the desired parabolic cross section, with the maximum radiation dosage at the origin, and zero dosage at (Y=$-Y_0$).

Once the two plates meet at the origin, the beam is completely blocked. The irradiation of the half of the treatment area for which Y is less than zero is complete for the second half of the treatment (with X=a constant).

During the last portion of the irradiation, plate 13 is held motionless at the origin, while plate 14 moves away from plate 13 in the positive Y direction. The beam intensity during this part of the treatment is again controlled to follow equation (5). The last portion of the irradiation deposits a beam profile on the positive side of the Y axis, completing the desired parabolic cross section, with the maximum radiation dosage at the origin, and zero dosage at (Y=$+Y_0$). When plate 14 reaches the point (X=0, Y=+Y₀), the radiation is interrupted. The treatment is complete.

In these exemplary treatments, the processor 21 moves the plates 12a, 12b, 13 and 14 with fixed velocities and periodically determines desirable radiation beam intensities according to these equations. Radiation intensity is changed by controlling the rate at which electron pulses are emitted by the electron gun. During each of the described treatment schemes, only one of the plates 12a, 12b, 13 and 14 is in motion at any given time.

Alternatively, the intensity of the radiation beam may be held constant or allowed to vary in time according to a predetermined function during the treatment and the plates may be moved with velocities that are functions of time or of radiation intensity to produce a non-linear beam profile. To generate a rotationally symmetric beam profile, for example, the equations 4 and 5 may be solved for $v_x$ and $v_y$ and the beam intensity may be held constant. In this alternative embodiment, the processor 21 causes motor controller 18 and drive units 19 and 20 to periodically move the plates to positions which produce the desired velocity profile.

A second embodiment of the invention for depositing the desired parabolic isodose profile may be used to overcome hardware limitations on the radiation treatment apparatus which restricts the motion of the lower plates. In the second method, the lower plates may have limited ability to move, or they may even be fixed.

In this embodiment of the invention, the first interval of the composite treatment is performed with the lower plates 13, 14 fixed, while the intensity of the radiation beam and the motion of plates 12a, 12b defined by equation (4), as in the first embodiment. At the completion of the first half of the treatment, the radiation is interrupted, the upper plates 12a, 12b are returned to their original positions, and the lower plates 13, 14 remain open. The lower part of collimator assembly 105 is rotated ninety degrees by the drive unit 22 responsive to the processor 21, so that the upper plates 12a, 12b are positioned along the Y axis, and the lower plates are symmetrically placed about the X axis. The second interval of the composite treatment follows the beam intensities and plate motions governed by equation (5), as in the first embodiment. In this second half of the treatment, however, it is the plates 12a and 12b which are moved.

The second embodiment may have advantages over the first embodiment for a beam forming apparatus with a rotatable collimator. Because the upper plates are closer to the radiation source, movement of an upper plate effects a greater change in the width of the beam (in the plane of the treatment area) than does movement of a lower plate through the same distance. Since the upper 12a, 12b and lower 13, 14 plates are typically actuated by the same type of equipment, they are each capable of being actuated at the same maximum plate velocity. Therefore, the upper plates 12a, 12b are capable of increasing or decreasing the width of the beam by a desired amount faster than the lower plates 13, 14 can. In addition, control of the apparatus may be simplified in a system having a rotating collimating assembly, since only one pair of numerically controlled drive units 19 is needed to actuate the one set of plates for this device.

It is understood by practitioners in the field that the parabolic isodose profiles realized by the above control schemes are exemplary in nature and that a number of variations are mathematically possible. The use of these parabolic contours, rotationally symmetric about the origin simplifies the plate movements used to achieve the desired isodose contours. For example, one or both of the parabolic contours could be offset from the origin by a constant displacement. This would require both plates in one or both sets of plates to be capable of crossing the axis. Although this is technically feasible, it is easier to move the object treated and keep the beam center at the origin than to electronically offset the beam profile center.

A third embodiment uses the general teachings of the earlier described embodiments to extend the capabilities of the invention even further. In this embodiment, the collimator 105 does not require a flattening filter 5. Instead, the motions of the collimator plates 12a, 12b, 13, 14 are controlled to produce a beam profile whose isodose contours are approximately flat. That is to say, any isodose contour will lie in a plane parallel to the treatment surface. Using this method, the radiation output of the electron accelerator is not decreased by filter attenuation, so that for a given accelerator, higher radiation intensity may be applied to the treatment area. This method may have many applications ranging from pencil beam treatment to whole body radiation.

Figure 4:
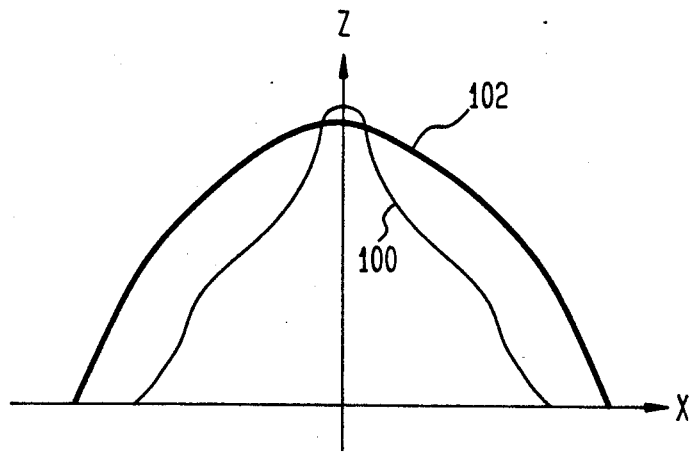

FIG. 4 shows the beam profile 100 produced with both collimator plates open, when the flattening filter 5 is removed (hereinafter referred to as the "raw beam" profile). The raw beam profile 100 may have an arbitrary form, and will vary with the apparatus used. This profile is empirically determined. For typical raw beams, this isodose curve may be approximated by finding a best-fit parabolic curve 102. The parabolic curve 102 is exaggerated in the Figure to clearly distinguish it from the raw beam profile 100. In order to apply a uniform dosage with the raw beam, it is necessary to expose the areas further from the origin to the beam longer than the center is exposed to the beam. That is to say, a compensating beam profile which is complementary to the parabolic isodose curve of raw beam 100 is needed.

Figure 5A:
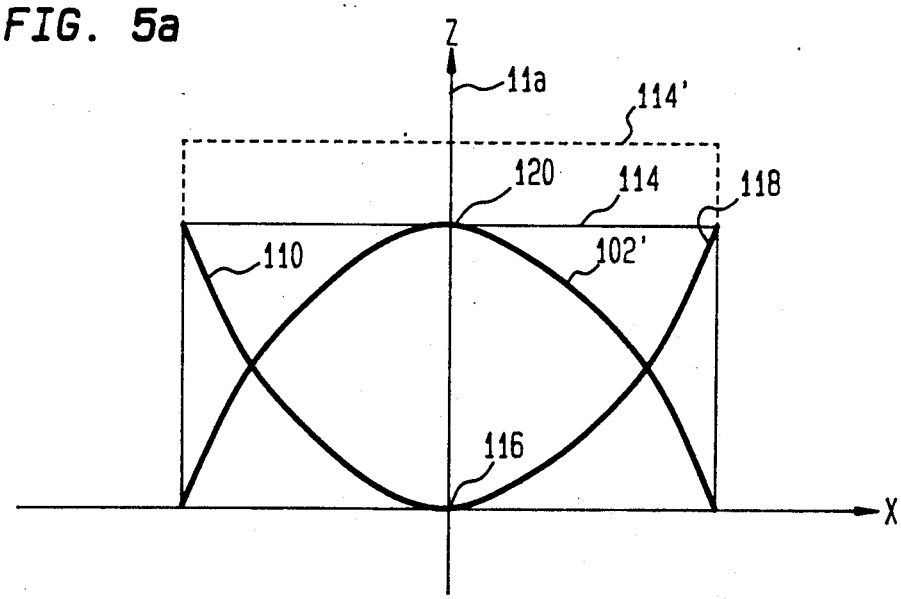

FIG. 5a shows how a compensating isodose curve 110 is added to the raw beam isodose curve 102' to provide a flat profile 114. FIG. 5 shows clearly that the compensating isodose curve 110 is greatest at the edges of the beam 118, and has a minimum at the beam axis 116. The smallest total flat beam isodose profile which may be achieved is the dose 120 detected at the beam axis 11a for the raw beam 102'. Mathematically, the compensating isodose profile 110 is the difference produced by subtracting the profile of the raw beam 102' from that of the flat beam 114. To produce this compensating beam profile 110, the compensating dosage profile at the edge of the beam is desirably the raw beam maximum value 120, and the compensating dosage must fall off to zero at the center 11a of the beam. The upper dose limit is determined by the maximum raw beam intensity 120 and the available plate speeds.

It is understood by one skilled in the art that a flat profile with a higher total dosage 114' may be achieved by extending the amount of time that the plates spend in any one position.

The inventors have determined that the relationship between the plate movements and the dosage rate for the dynamic generation of a flat beam profile is defined by equations (6) and (7).

$$\dot{D}_{01(x)}|_{y=const} = D_a\mu[e^{\mu(F-K+ay^2)}] * e^{\mu ax^2} 2axv_x \quad (6)$$
$$\dot{D}_{02(y)}|_{x=const} = D_a\mu[e^{\mu(F-K+ax^2)}] * e^{\mu ay^2} 2ayv_y \quad (7)$$

Figure 2A:
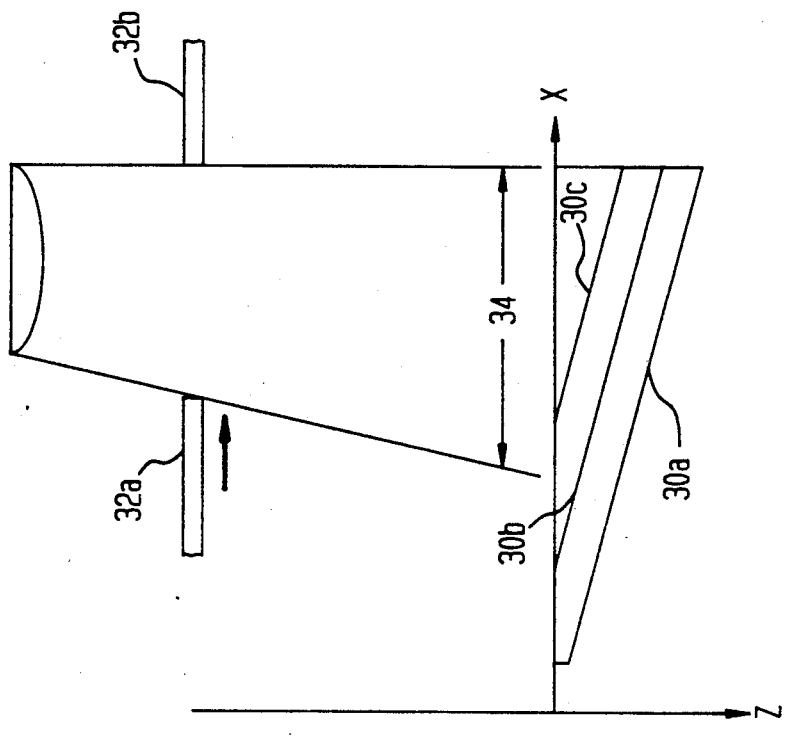
FIGS. 2a and 2b are graphs of radiation intensity versus distance which show typical wedge shaped isodose profiles produced by prior art systems.
Figure 2B:
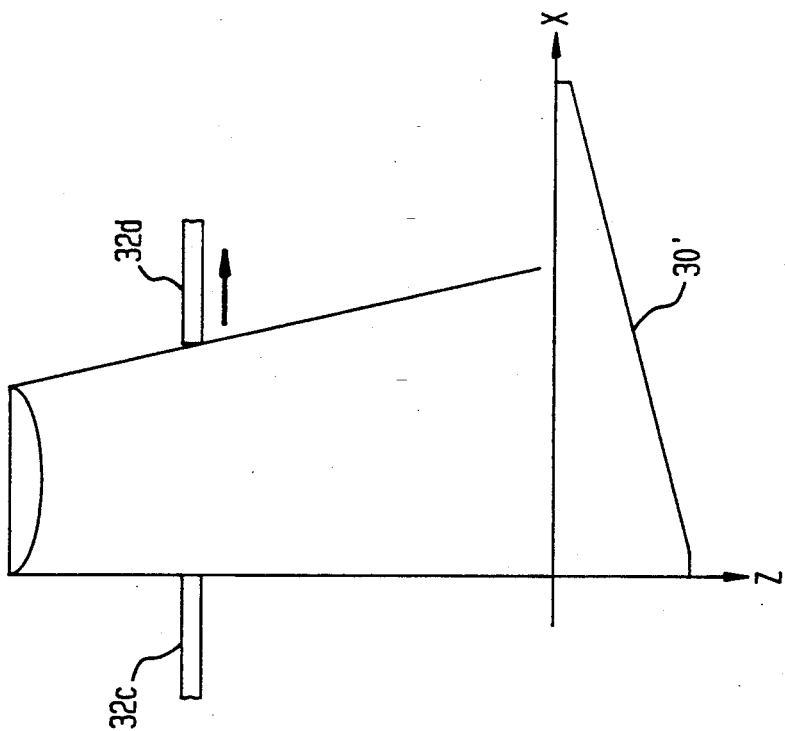
Figure 3A:
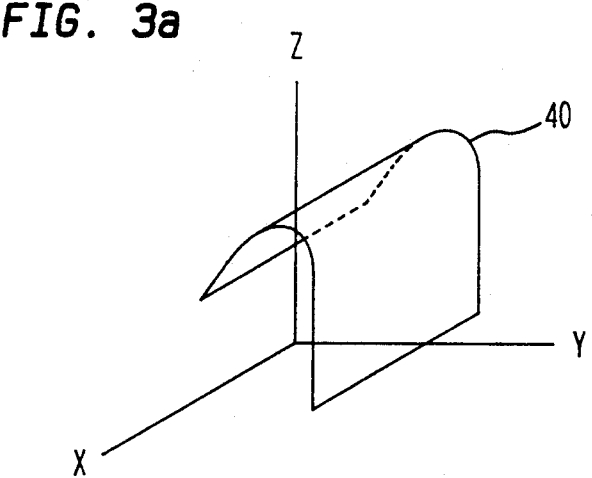
Figure 3B:
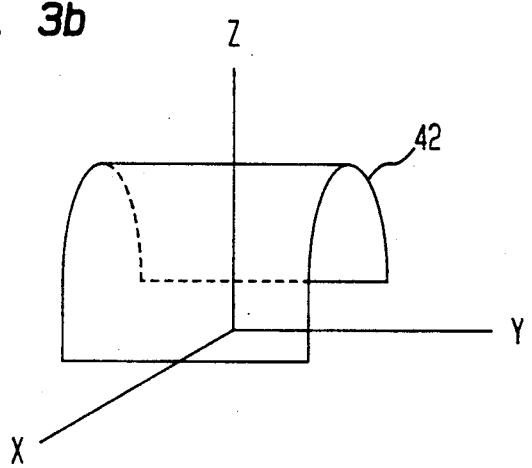
Figure 3C:
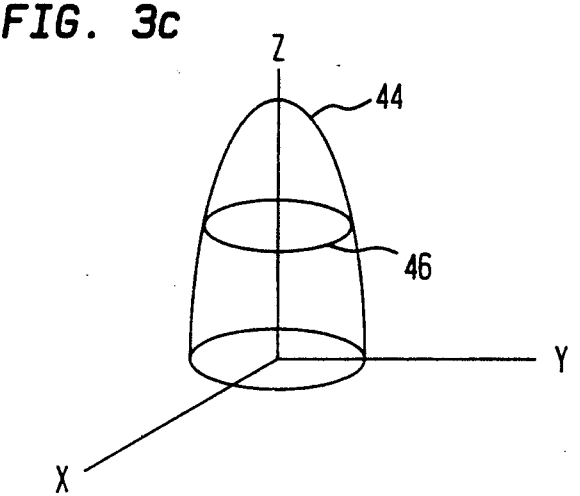
FIG. 3c is a graph of radiation intensity versus distance which shows the effective isodose profile formed by summing the profiles shown in FIGS. 3a and 3b.

As noted above, in order to move the collimator plates to furnish the beam profile defined by equations (6) and (7), the treatment area must be exposed to the edges of the beam longer than the center of the treatment area (at the beam axis). As shown in FIGS. 2a and 2b, during any dynamic beam forming treatment, the region under the stationary plate is exposed to the radiation the longest.

In contrast to the parabolic beamform generation in the first and second embodiments of the invention, flat beam generation shown in FIG. 5 requires that the stationary plate be positioned at the outer edge of the beam instead of at the beam center. In order to accomplish this, both plates in at least one set of collimator plates 12a, 12b are capable of crossing the axis.

In order to apply the treatment, the apparatus is first set up with the lower collimator plates 13, 14 positioned at edges of the beam field symmetrically placed about the X axis at coordinates (X=0, Y=−Y₀) and (X=0, Y=+Y₀), respectively, where Y₀ is a constant. These plates are held steady during the first section of the treatment.

Figure 5B:
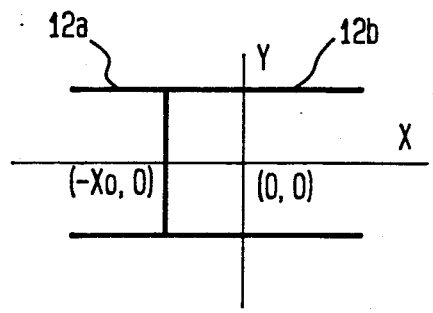

As shown in FIG. 5b, upper plates 12a and 12b are both initially placed along the X axis at (X=−X₀, Y=0). Plate 12a is held motionless at the edge of the desired beam, while Plate 12b is actuated towards the origin, increasing the width of the beam. During this portion of the treatment, the intensity of the beam is governed by equation (6).

Once plate 12b reaches the origin, the treatment is interrupted. The irradiation of the portion of the treatment area for which X is less than zero and Y is a constant is complete.

Figure 5C:
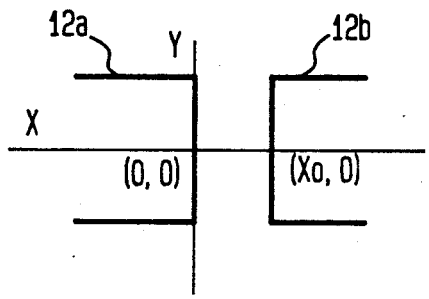

Next, as shown in FIG. 5c, plate 12a is positioned at the origin and plate 12b is moved to (X=+X₀, Y=0) before beginning the next portion of the treatment.

During the next portion of the irradiation, plate 12b is held motionless, while plate 12a moves towards 12b in the positive X direction, decreasing the beam width. The beam intensity during this part of the treatment is again controlled to follow equation (6). The second portion of the irradiation deposits a beam profile on the positive side of the X axis, completing the desired flat beam. When plate 12b reaches the point (X=+X₀, Y=0), the plates have closed and the radiation is interrupted. The first half of the treatment, in which the positions of plates 13, and 14 are held constant, is complete. It should be noted that both plates 12a and 12b cross the beam axis during the first half of the treatment.

The upper plate 12a is returned to (X=−X₀, Y=0), "fully opening" the upper plates. As in the first half of the treatment, the motionless plates are only opened up enough to irradiate the zone to be treated, and surrounding tissues are not subjected to irradiation. Lower plates 13 and 14 are both moved to (X=0, Y=−Y0) a closed position, prior to beginning the second half of the irradiation.

From this point on, the half of the treatment with the upper plates fixed proceeds similarly to the treatment with the lower plates still. Plate 13 is held motionless at the edge of the beam, while Plate 14 is actuated away from plate 13. During this portion of the treatment, the intensity of the beam is governed by equation (7). The isodose contour has the desired flat profile.

Once the plate 14 reaches the origin, the treatment is interrupted. The irradiation of the half of the treatment area for which Y is less than zero and X is constant is complete. Plate 13 is moved to the origin and plate 14 is moved to the edge of the beam at (X=+X₀, Y=0) before resuming treatment.

During the last portion of the irradiation, plate 14 is held motionless, while plate 13 moves towards plate 13 in the positive Y direction. The beam intensity during this part of the treatment is again controlled to follow equation (7). The last portion of the irradiation deposits a flat beam profile on the positive side of the Y axis, completing the treatment. The result is that the isodose contour has the desired flat profile.

It is understood by one skilled in the art that a flat profile with a higher total dosage 114' may be achieved by reducing the velocities $v_x$ and $v_y$ resulting in the plates being held in each position for a longer period of time.

Furthermore, it should be understood by those skilled in the art that other movements of the aperture plates could produce the same result. For example, in FIG. 5c, both plates 12a and 12b could start at position 0, +X₀ and plate 12a could be moved away from plate 12b.

It is understood by one skilled in the art that a flat profile with a higher total dosage 114' may be achieved by reducing the velocities $v_x$ and $v_y$ resulting in the plates being held in each position for a longer period of time.

It is understood by one skilled in the art that many variations of the embodiments described herein are contemplated. While the invention has been described in terms of exemplary embodiments, it is contemplated that it may be practiced as outlined above with modifications within the spirit and scope of the appended claims.

The invention claimed is:

1. A system for controlling the application of a radiation treatment to an object, comprising:
   a radiation source which generates a radiation beam having a path to the object which defines an axis, said radiation source applying said beam to said object;
   a collimator, having a plurality of movable plates disposed in the path of the radiation beam and oriented in a direction perpendicular to said beam axis;
   means for actuating each of the plurality of movable plates independently while applying the radiation to vary the portion of the object being irradiated, responsive to an actuator control signal, wherein the beam applied to the object changes in width when the plates are so actuated; and
   means for rotating the collimator, responsive to a rotation control signal;
   means for providing the actuator control signals and rotation control signals;
   wherein separate radiation doses are applied, during a first interval before the collimator is rotated and during a second interval after the collimator is rotated, to produce a composite radiation dose distribution.

2. The system set forth in claim 1, wherein the plate actuating means further comprises:
   means for actuating a first one of said plates and keeping a second one of said plates stationary while applying the radiation; and means for actuating both first and second plates in a common direction during the treatment.

3. The system set forth in claim 1, wherein the plate actuating means further comprises:
means for actuating a first one of said plates and keeping a second one of said plates stationary while applying the radiation; and
means for actuating both first and second plates in a common direction during said first interval and in a further common direction during said second interval.

4. The system set forth in claim 1, wherein the plate actuating means further comprises means for actuating a first and second of said plates in a common direction during the treatment, wherein each plate moves from one side of the beam axis to another side of the beam axis during the treatment.

5. A system according to claim 1, in which the beam has an intensity, further comprising:
means for controlling the radiation beam to vary the beam intensity while applying the radiation in response to a control voltage signal;
means for determining the instantaneous position of at least one of the plurality of movable plates; and
means for generating the control voltage signal as a function of the determined instantaneous positions of the plurality of movable plates to produce a desired dosage profile.

6. A system according to claim 5, wherein:
the radiation source includes an electron gun and a wave guide; and
the means for controlling the radiation beam includes a pulse generator which applied pulses having substantially equal amplitudes at pulse rates controlled by the control voltage signal to the electron gun to cause the electron gun to provide pulses of electrons to the wave guide.

7. A method for controlling the application of a radiation treatment to an object in a system having a radiation source generating a radiation beam with a path to the object which defines an axis, said radiation source being attached a collimator having a plurality of movable plates disposed in the path of the radiation beam, and oriented in a direction perpendicular to said beam axis, the method comprising the steps of:
a) generating an actuator control signal and a rotation control signal;
b) actuating the plates independently while applying the radiation to vary the portion of the object being irradiated, in response to the actuator control signal, wherein the beam changes in width when the plates are so actuated; and
c) rotating the collimator during an interruption in the treatment, in response to the rotation control signal, wherein separate radiation doses are applied, during a first interval before the collimator is rotated and during a second interval after the collimator is rotated, to produce a composite radiation dose distribution.

8. The method set forth in claim 7, wherein the step of rotating the collimator includes a ninety degree collimator rotation.

9. The method set forth in claim 7, wherein step (b) further comprises the step of actuating two plates in a common direction during the treatment, wherein each of said two plates moves from one side of the beam axis to another side of the beam axis during the treatment.

10. The method set forth in claim 7, wherein step (b) further comprises the step of actuating two plates in a common direction during the treatment, wherein each plate moves from one side of the beam axis to another side of the beam axis during each respective interval.

11. A system for controlling the application of a radiation treatment to an object, comprising:
a radiation source including an electron gun which is responsive to a pulse signal, having a pulse rate, to generate a radiation beam having a path to said object which defines an axis, said radiation source applying said beam to said object;
a collimator, having a plurality of movable plates disposed in the path of the radiation beam and oriented perpendicular to said beam axis;
means for actuating each of the plurality of movable plates independently while applying the radiation to vary the portion of the object being irradiated, responsive to an actuator control signal, wherein the beam applied to the object changes in width, as the plates are so actuated; and
means for rotating the collimator, responsive to a rotation control signal;
means for changing the intensity of the radiation beam produced by the radiation source while applying the radiation, by changing the pulse rate of the pulse signal in response to a control voltage signal;
means for providing the actuator control signal, rotation control signal and control voltage signal to produce a predetermined radiation treatment profile.

12. A system according to claim 11, further comprising:
means for determining the instantaneous position of at least one of the plurality of movable plates; and
means for generating the control voltage signal as a function of the determined instantaneous positions of the plurality of movable plates to produce a desired dosage profile.

13. A system according to claim 12, wherein:
the radiation source includes an electron gun and a wave guide; and
the means for controlling the radiation beam includes a pulse generator which applies pulses having substantially equal amplitudes at pulse rates controlled by the control voltage signal to the electron gun to cause the electron gun to provide pulses of electrons to the wave guide.

* * * * *